United States Patent
Yamada et al.

(10) Patent No.: US 9,500,581 B2
(45) Date of Patent: Nov. 22, 2016

(54) BLOOD ANALYZER AND BLOOD ANALYZING METHOD

(71) Applicant: Sysmex Corporation, Kobe-shi, Hyogo (JP)

(72) Inventors: Kazuhiro Yamada, Kobe (JP); Kazuhiro Sasaki, Kobe (JP)

(73) Assignee: SYSMEX CORPORATION, Kobe-Shi (JP)

(*) Notice: Subject to any disclaimer, the term of this patent is extended or adjusted under 35 U.S.C. 154(b) by 0 days.

(21) Appl. No.: 14/866,246

(22) Filed: Sep. 25, 2015

(65) Prior Publication Data

US 2016/0091424 A1 Mar. 31, 2016

(30) Foreign Application Priority Data

Sep. 26, 2014 (JP) .................................. 2014-196280

(51) Int. Cl.
| | |
|---|---|
| *G01N 33/48* | (2006.01) |
| *G01N 21/53* | (2006.01) |
| *G01N 15/14* | (2006.01) |
| *G01N 33/49* | (2006.01) |
| G01N 15/00 | (2006.01) |
| G01N 15/10 | (2006.01) |

(52) U.S. Cl.
CPC .......... *G01N 21/53* (2013.01); *G01N 15/1459* (2013.01); *G01N 33/4915* (2013.01); *G01N 2015/0073* (2013.01); *G01N 2015/1006* (2013.01); *G01N 2015/1477* (2013.01); *G01N 2800/22* (2013.01)

(58) Field of Classification Search
CPC .............. G01N 21/6428; G01N 2021/6439; G01N 21/6486; G01N 21/3563; G01N 15/1475; G01N 33/54373; G01N 1/2813; G01N 1/312; G01N 33/49; G01N 35/00029; G01N 21/255; G01N 2201/062; G01N 2201/126

See application file for complete search history.

(56) References Cited

U.S. PATENT DOCUMENTS

| | | | |
|---|---|---|---|
| 4,735,504 A | 4/1988 | Tycko | |
| 5,194,909 A | 3/1993 | Tycko | |
| 6,630,990 B2 | 10/2003 | van't Oever et al. | |
| 2008/0268494 A1* | 10/2008 | Linssen .................. | G01N 15/12 435/39 |
| 2008/0283754 A1* | 11/2008 | Nerin ................... | G01N 15/147 250/339.05 |
| 2010/0273168 A1* | 10/2010 | Krockenberger ...... | G01N 15/00 435/6.12 |
| 2012/0296570 A1* | 11/2012 | Merchez ............ | G01N 15/1436 702/19 |

FOREIGN PATENT DOCUMENTS

| | | |
|---|---|---|
| JP | H08-20442 A | 1/1996 |
| JP | H11-326315 A | 11/1999 |

OTHER PUBLICATIONS

Shapiro, "Multiple Wavelength Scattering Measurements", *Practical Flow Cytometry*, Wiley-liss, 1995, 4 pages.

* cited by examiner

*Primary Examiner* — Michael P Stafira
(74) *Attorney, Agent, or Firm* — Brinks Gilson & Lione

(57) ABSTRACT

A blood analyzer comprises a flow cell, a first light source, a second light source, a first light receiving part, a second light receiving part, and a processing unit. The processing unit is configured to make determinations related to the types of microcytic anemia based on a first scattered light information based on the signals output from the first light receiving part, and a second scattered light information based on the signals output from the second light receiving part.

16 Claims, 14 Drawing Sheets

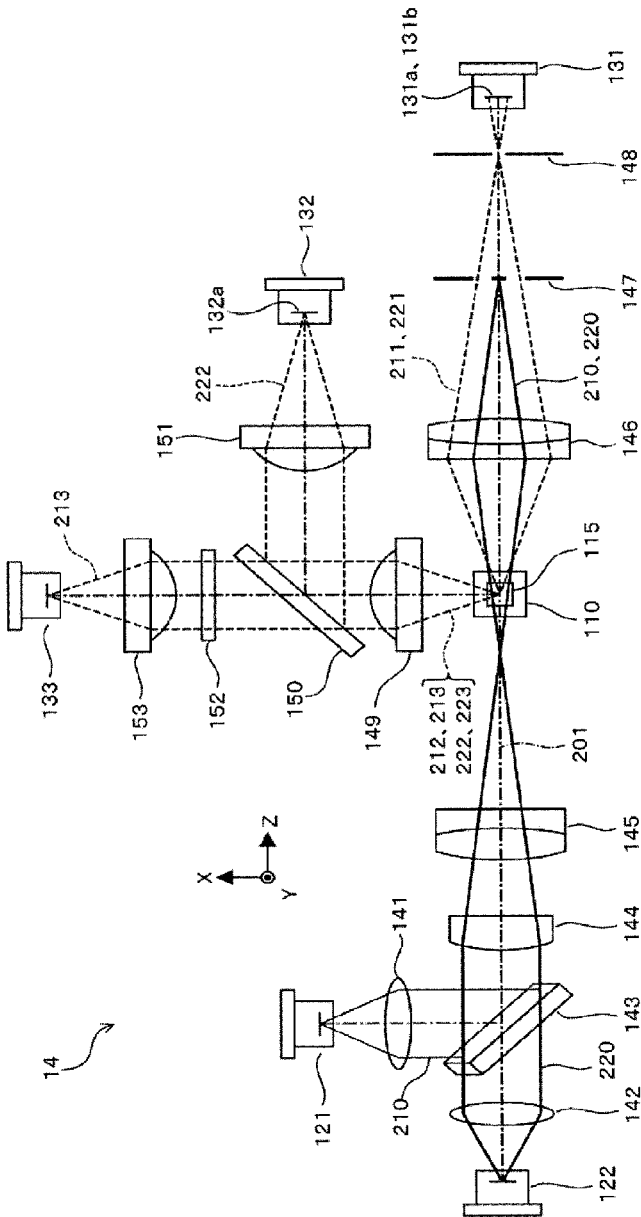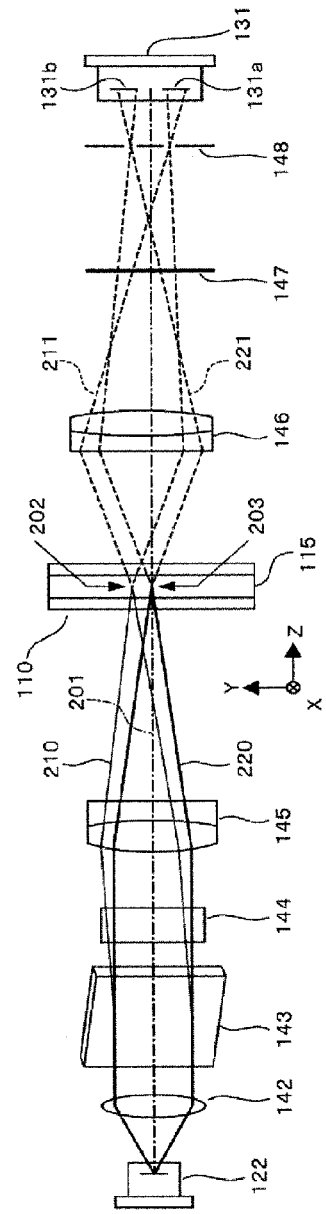
FIG. 2A
FIG. 2B

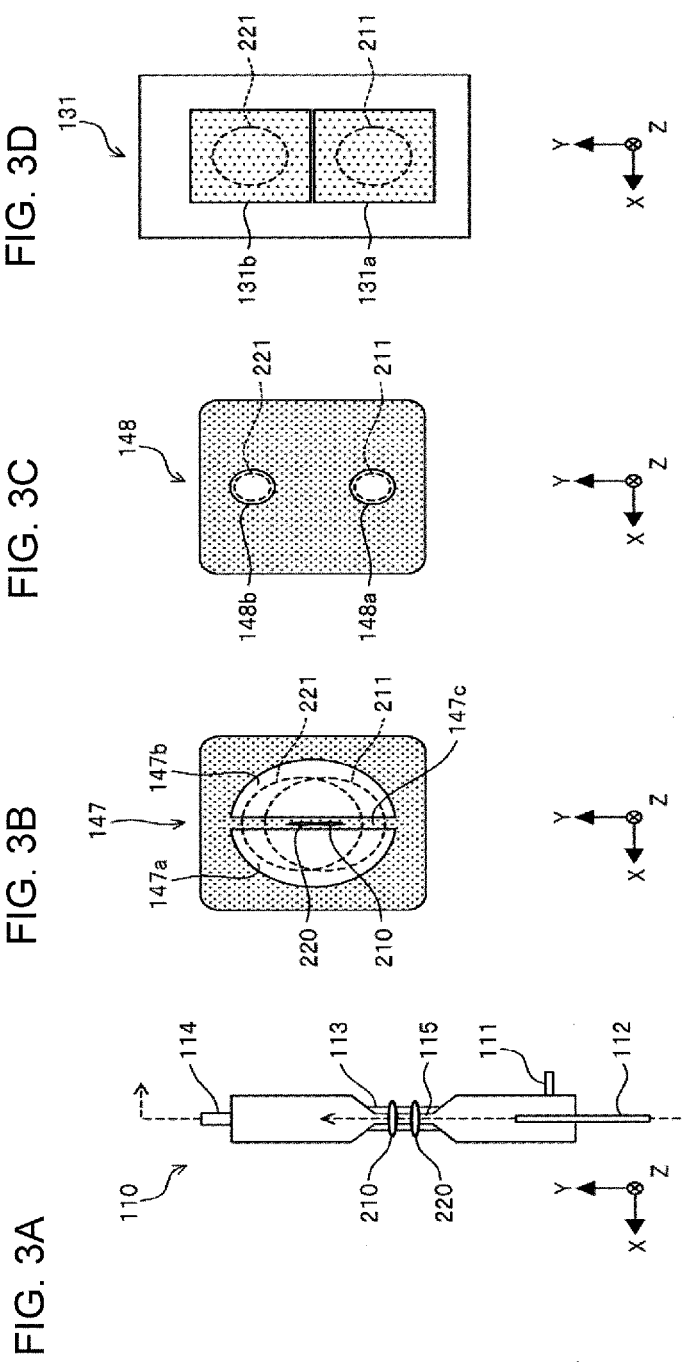

Normal

Iron deficiency anemia

Alpha-thalassemia

Beta-thalassemia

Normal

Iron deficiency anemia

Alpha-thalssemia

Beta-thalassemia

Hemoglobin concentration

BLOOD ANALYZER AND BLOOD ANALYZING METHOD

RELATED APPLICATIONS

This application claims priority from prior Japanese Patent Application No. 2014-196280 filed on Sep. 26, 2014, entitled "BLOOD ANALYZER AND BLOOD ANALYZING METHOD".

BACKGROUND OF THE INVENTION

1. Field of the Invention

The present invention relates to a blood analyzer and a blood analyzing method.

2. Description of the Related Art

There are various types of anemia. Macrocytic anemia, normocytic anemia, and microcytic anemia are known as the broadest classifications of anemia. Iron deficiency anemia and thalassemia are known as anemias classified as microcytic anemia. Approximately 50% of anemia is iron deficiency anemia. The type of anemia the patient has must be accurately ascertained for medication and treatment of the anemia patient.

Japanese Patent Application Publication No. 11-326315 discloses a method of discriminating iron deficiency anemia and thalassemia among microcytic anemias using the measured values of CBC items which are basic measurement items performed by blood cell counters. In this method iron deficiency anemia and thalassemia are discriminated based on the values of CBC measurement items.

However, since iron deficiency anemia and thalassemia have similar measurement values of CBC measurement items, it is difficult to improve the discrimination accuracy among the types of microcytic anemias by a discrimination method which used the measurement values of CBC measurement items.

SUMMARY OF THE INVENTION

The scope of the present invention is defined solely by the appended claims, and is not affected to any degree by the statements within this summary.

The blood analyzer of a first aspect of the present invention is provided with a flow cell configured to flow a measurement sample containing blood cells, a first light source configured to irradiate light having a first wavelength on the measurement sample flowing through the flow cell, a second light source configured to irradiate a second light having a second wavelength which is different from the first wavelength on the measurement sample flowing through the flow cell, a first light receiving part configured to receive a first scattered light obtained by irradiating the first light on the blood cells flowing through the flow cell, a second light receiving part configured to receive a second scattered light obtained by irradiating the second light on the blood cells flowing through the flow cell, a processing unit configured to make determinations regarding microcytic anemia based on a first scattered light information which is based on the signals output from the first light receiving part, and a second scattered light information which is based on the signals output from the second light receiving part.

The blood analyzing method of a second aspect of the present invention includes irradiating a first light having a first wavelength and irradiating a second light having a second wavelength which is different from the first wavelength on a measurement sample containing blood cells, receiving a first scattered light obtained by irradiating the first light on a blood cell, and receiving a second scattered light obtained by irradiating the second light on the blood cell, and making determinations regarding types of microcytic anemia based on the first scattered light information which is based on the first scattered light, and the second scattered light information which is based on the second scattered light.

Effects of the Invention

According to the present invention, it is possible to discriminate types of microcytic anemia with greater accuracy because analysis is based on information obtained from each individual blood cell.

BRIEF DESCRIPTION OF THE DRAWINGS

FIG. 2A and FIG. 2B respectively are schematic views of the optical detection unit of the first embodiment viewed in the Y-axis negative direction and the X-axis positive direction;

FIG. 3A through FIG. 3D respectively are schematic views showing the structure of the flow cell, beam stopper, pinhole, and optical detection unit of the first embodiment;

DETAILED DESCRIPTION OF THE PREFERRED EMBODIMENTS

The first through third embodiments described below apply the present invention in an apparatus which performs examination and analysis of blood by detecting the red blood cells and the like contained in a blood sample, and counting each blood cell.

First Embodiment

Figure 1:
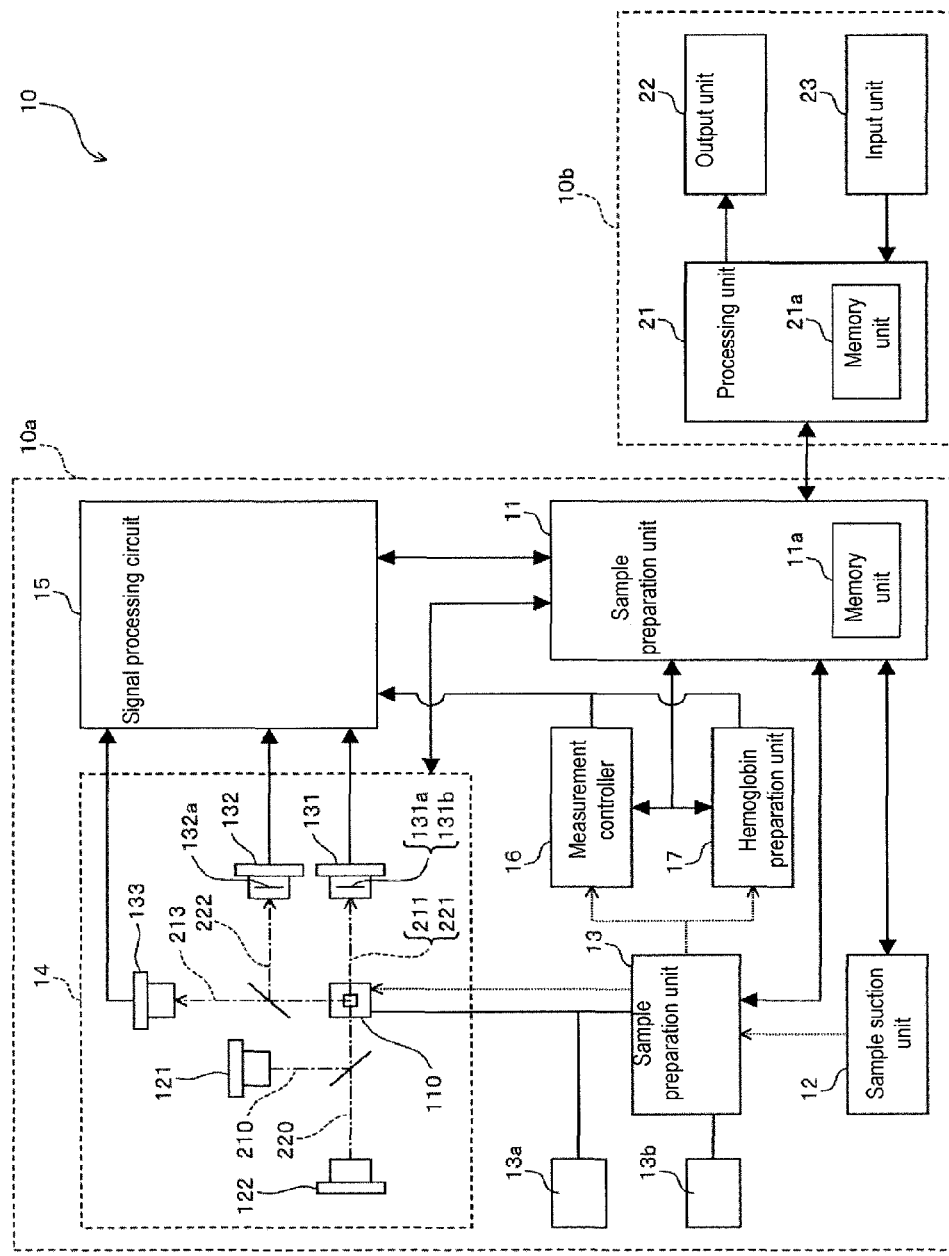
FIG. 1 is a block diagram showing the structure of the blood analyzer of a first embodiment.

As shown in FIG. 1, a blood analyzer 10 is provided with a measuring unit 10a and an information processing unit 10b. The measuring unit 10a is provided with a measurement controller 11, sample suction unit 12, sample preparing unit 13, optical detection unit 14, and signal processing circuit 15, electrical resistance type detection unit 16, and hemoglobin detection unit 17. The measurement controller 11 has a memory unit 11a. The information processing unit 10b is provided with a processing unit 21, output unit 22, and input unit 23. The processing unit 21 has a memory unit 21a.

The measurement controller 11 receives signals output from each part of the measuring unit 10a, and controls each part of the measuring unit 10a. The measurement controller 11 performs communications with the information processing unit 10b. The sample suction unit 12 suctions the blood sample from the sample container through a suction tube. A container holding reagent 13a and a container holding reagent 13b are connected to the sample preparing unit 13. The reagent 13a is a diluting liquid. Reagent 13a is used as a sheath fluid to form the flow the measurement sample in the sheath flow cell of the electrical resistance detection unit 16. Reagent 13b is a hemolytic agent.

The sample preparing unit 13 mixes the reagent 13a and the blood sample suctioned by the sample suction unit 12 to prepare the first measurement sample to be used in measurements by the optical detection unit 14. The shape of red blood cells in the prepared first measurement sample becomes spherical through the reagent 13a. The sample preparing unit 13 mixes the reagent 13a and the blood sample suctioned by the sample suction unit 12 to prepare the second measurement sample to be used in measurements by the electrical resistance detection unit 16. The preparation of the first and second measurement samples is performed without using hemolytic agent and stain. The first and second measurement samples contain the blood cells in the blood sample. The sample preparing unit 13 mixes the reagents 13a, 13b and the blood sample suctioned by the sample suction unit 12 to prepare the third measurement sample to be used in measurements by the hemoglobin detection unit 17.

Optical detection unit 14 has a flow cell 110, first light source 121, second light source 122, and optical detectors 131 through 133. The first light source 121 irradiates a first light 210 having a first wavelength on the first measurement sample flowing through the flow cell 110. The second light source 122 irradiates a second light 22 having a second wavelength which is different from the first wavelength on the first measurement sample flowing through the flow cell 110.

The optical detector 131 has a first light receiving part 131a and a second light receiving part 131b. The first light receiving part 131a receives a first scattered light obtained by irradiating the first light 210 on a blood cell flowing through the flow cell 110. The first scattered light is a first forward scattered light 211 in the first embodiment. The second light receiving part 131b receives a second scattered light obtained by irradiating the second light 220 on a blood cell flowing through the flow cell 110. The second scattered light is a second forward scattered light 221 in the first embodiment. The optical detector 132 has a light receiving part 132a. The light receiving part 132a receives a second side scattered light 222 obtained by irradiating the second light 220 on a blood cell flowing through the flow cell 110. The optical detector 133 receives a first fluorescent light 213 obtained by irradiating the first light 210 on a blood cell flowing through the flow cell 110.

The first scattered light also may be the first side scattered light 212 which is described below. That is, the first light receiving part 131a also may be arranged so as to receive the first side scattered light 212 as the first scattered light. The second scattered light also may be the second side scattered light 222. That is, the second light receiving part 131b also may be arranged so as to receive the second side scattered light 222 as the second scattered light.

The first light receiving part 131a outputs signals based on the first forward scattered light 211. The second light receiving part 131b outputs signals based on the second forward scattered light 221. The optical detector 131 sends the signals output from the first light receiving part 131a and the second light receiving part 131b to the signal processing circuit 15. The light receiving part 132a outputs signals based on the second side scattered light 222. The optical detector 132 sends the signals output from the light receiving part 132a to the signal processing circuit 15. The optical detector 133 sends the signals based on the first fluorescent light 213 to the signal processing circuit 15. The optical detection unit 14 is described below with reference to FIG. 2A and FIG. 2B and FIG. 3A through FIG. 3D.

The electrical resistance detection unit 16 measured blood cells by a sheath flow-DC method. The second measurement sample is supplied from the sample preparing unit 13 to the electrical resistance detection unit 16. The electrical resistance detection unit 16 applies a voltage to the second measurement sample flowing through the sheath flow cell, and detects the blood cell by detecting the change in voltage produced by the passage of the blood cell. The electrical resistance detection unit 16 outputs the detection signal to the signal processing circuit 15.

The hemoglobin detection unit 17 measures the amount of hemoglobin by a hemoglobin method. The third measurement sample is supplied from the sample preparing unit 13 to the hemoglobin detection unit 17. The hemoglobin detection unit 17 irradiates light having a wavelength of 555 nm on the third measurement sample held in the cell. The hemoglobin detection unit 17 outputs the detection signal to the signal processing circuit 15.

The signal processing circuit 15 extracts the waveforms corresponding to blood cells, and calculates the peak values, widths, areas and the like of the waveforms based on the signals output by the optical detectors 131 through 133. The signal processing circuit 15 calculates the peak value of the waveform obtained from the signal based on the first forward scattered light 211 as the first scattered light information. The signal processing circuit 15 calculates the peak value of the waveform obtained from the signal based on the second forward scattered light 221 as the second scattered light information. The signal processing circuit 15 calculates the peak value of the waveform obtained from the signal based on the second side scattered light 222 as the third scattered light information. The signal processing circuit 15 calculates the peak value of the waveform obtained from the signal based on the first fluorescent light 213 as the fluorescent light information. The signal processing circuit 15 extracts the waveforms corresponding to blood cells, and calculates the peak values of the waveforms as blood cell information based on the signals output by the electrical resistance detection unit 16. The signal processing circuit 15 converts the signals output from the hemoglobin detection unit 17 to the amount of hemoglobin.

When the first scattered light is designated as the first side scattered light 212, the first scattered light information becomes the peak value of the waveform obtained from the signals based on the first side scattered light 212. When the second scattered light is designated as the second side scattered light 222, the second scattered light information becomes the peak value of the waveform obtained from the signals based on the second side scattered light 222.

The signal processing circuit 15 outputs the first scattered light information, second scattered light information, third scattered light information, fluorescent light information, blood cell information, and hemoglobin content to the measurement controller 11. The measurement controller 11 stores the information output from the signal processing circuit 15 in a memory unit 11a. When the blood sample measurements end, the measurement controller 11 sends the first scattered light information, second scattered light information, third scattered light information, fluorescent light information, blood cell information and hemoglobin content obtained for each blood cell to the information processing unit 10b as measurement data.

The processing unit 21 receives signals output from each part of the information processing unit 10b, and controls each part of the information processing unit 10b. The memory unit 21a stores a program which is executed by the processing unit 21, and various data. The memory unit 21a also is used as the work area of the processing unit 21. The processing unit 21 makes determinations related to types of microcytic anemia based on the first scattered light information and the second scattered light information. The processing unit 21 additionally classifies and counts the blood cells and obtains various values. The processes performed by the processing unit 21 are described below referring to FIG. 8A.

The output unit 22 is a display which displays textual and graphic information. The input unit 23 is a keyboard and mouse which receive input from the operator.

As shown in FIG. 2A and FIG. 2B, the optical detection unit 14 is provided with a flow cell 110, first light source 121, second light source 122, optical detectors 131 through 133, collimator lenses 141 and 142, dichroic mirror 143, cylindrical lens 144, collective lenses 145 and 146, beam stopper 147, pinhole 148, collimator lens 149, dichroic mirror 150, collective lens 151, spectral filter 152, and collective lens 153. For the sake of convenience, the mutual intersection of the XYZ coordinate axes is shown in FIG. 2A and FIG. 2B.

As shown in FIG. 3A, the flow cell 110 has a sheath fluid supply port 111, a sample nozzle 112, a pore part 113, and a disposal port 114. The sheath fluid supply port 111 supplies sheath fluid into the flow cell 110. The sample nozzle 112 injects a measurement sample in the Y-axis positive direction within the flow cell 110. The first measurement sample progresses through a flow path 115 formed in the pore part 113 while encapsulated in the sheath fluid, and toward the disposal port 114. The flow path 115 extends in the Y-axis direction. The particles contained in the first measurement sample pass through the flow path 115 in single file array.

Returning to FIG. 2A and FIG. 2B, the first light source 121 emits a first light 210 in the X-axis negative direction. The first light 210 is laser light. The wavelength of the first light 210 is set at 400 nm or greater but not more than 435 nm. In the first embodiment, the wavelength of the first light 210 is approximately 405 nm. The first light source 121 is arranged so that the lamination direction of the semiconductor layers of the light emitting part (not shown in the drawing) matches the Z-axis direction. The spread angle of the first light 210 is greatest in the Z-axis direction and smallest in the Y-axis direction. The exit optical axis of the first light source 121 intersects the optical axis 201 of the collimator lens 142. The optical axis 201 is parallel to the Z-axis.

The second light source 122 emits the second light 220 in the Z-axis positive direction. The second light 220 is laser light. The wavelength of the second light 220 is set at 610 nm or greater but not more than 750 nm. In the first embodiment, the wavelength of the second light 220 is approximately 640 nm. The second light source 122 is arranged so that the lamination direction of the semiconductor layers of the light emitting part (not shown in the drawing) matches the X-axis direction. The spread angle of the second light 220 is greatest in the X-axis direction and smallest in the Y-axis direction. The exit optical axis of the second light source 122 matches the optical axis 201.

The collimator lens 141 converts the first light 210 to parallel light. The collimator lens 142 converts the second light 220 to parallel light. The dichroic mirror 143 reflects the first light 210 and transmits the second light 220.

The dichroic mirror 143 is arranged so that the travel direction of the first light 210 reflected by the dichroic mirror 143 is inclined from the Z-axis direction slightly to the Y-axis direction, as shown in FIG. 2B.

The cylindrical lens 144 converges the first light 210 and second light 220 only in the X-axis direction. The collecting lens 145 converges the first light 210 and the second light 220 in the Y-axis direction, focusing on the position of the flow path 115 of the flow cell 110. The collecting lens 145 also converges the first light 210 and the second light 220 in the X-axis direction, focusing on the position on the Z-axis negative side of the flow path 115. Thus, the first light 210 and the second light 220 irradiate a narrow beam in the X-axis direction on the flow path 115, as shown in FIG. 3A.

As shown in FIG. 2B, since the first light 210 which is reflected by the dichroic mirror 143 travels in a direction slightly inclined from the Z-axis direction to the Y-axis direction, the irradiation position 202 of the first light 210 on the flow path 115 is shifted in the Y-axis positive direction from the irradiation position 203 of the second light 220. The irradiation position 203 of the second light 220 is on the optical axis 201.

When the first light 210 irradiates the blood cell at irradiation position 202, a first forward scattered light 211, first side scattered light 212, and first fluorescent light 213 are produced from the blood cell irradiated by the first light 210. The wavelength of the first forward scattered light 211 and the wavelength of the first side scattered light 212 are substantially the same as the wavelength of the first light 210. When the second light 220 irradiates the blood cell at irradiation position 203, a second forward scattered light 221, second side scattered light 222, and second fluorescent light 223 are produced from the blood cell irradiated by the second light 220. The wavelength of the second forward scattered light 221 and the wavelength of the second side scattered light 222 are substantially the same as the wavelength of the second light 220.

The collective lens 146 has the function of correcting chromatic aberration relative to the first forward scattered light 211 and the second forward scattered light 221. The collective lens 146 converges the first forward scattered light 211 and the second forward scattered light 221 at the position of the pinhole 148. The collective lens 146 also converges part of the first light 210 and the second light 220 that does not irradiate a blood cell and is transmitted through the flow cell 110 at the position of the beam stopper 147. As shown in FIG. 2B, the optical axis of the collective lens 146 is parallel to the Z-axis, that is, shifted in the Y-axis positive direction from the optical axis 201. Thus, after the light rays at the center of the first forward scattered light 211 are transmitted through the collective lens 146, the rays travel in a direction inclined slightly in the Y-axis negative direction from the Z-axis positive direction. After the light rays at the center of the second forward scattered light 221 are transmitted through the collective lens 146, the rays travel in a direction inclined slightly in the Y-axis positive direction from the Z-axis positive direction.

As shown in FIG. 3B, the beam stopper 147 has apertures 147a and 147b, and a light shield part 147c. The apertures 147a and 147b are semicircular in shape. The light shield part 147c is formed between the aperture 147a and the aperture 147b. The beam stopper 147 is configured by a thin plate member which is impenetrable to light. The beam stopper 147 is arranged at the focus position in the X-axis direction of the first light 210 and the second light 220. Thus, the first light 210 and the second light 220 become narrow beam shapes in the Y-axis direction on the light shield part 147c, and are blocked by the light shield part 147c. The majority of the first forward scattered light 211 and the second forward scattered light 221 pass through the beam stopper 147 through the apertures 147a and 147b.

As shown in FIG. 3C, the pinhole 148 has two holes 148a and 148b aligned in the Y-axis direction. The first forward scattered light 211 converges at the position of the hole 148a, and the second forward scattered light 221 converges at the position of the hole 148b. The first forward scattered light 211 and the second forward scattered light 221 pass through the holes 148a and 148b, respectively.

As shown in FIG. 3D, the optical detector 131 is a photodiode. The first light receiving part 131a and the second light receiving part 131b are arranged on the same plane. The optical detector 131 outputs signals based on the first forward scattered light 211 which irradiates the first light receiving part 131a, and signals based on the second forward scattered light 221 which irradiates the second light receiving part 131b.

Returning to FIG. 2A, the collimator lens 149 converts the first side scattered light 212, second side scattered light 222, first fluorescent light 213, and second fluorescent light 223 to parallel light. The optical axis of the collimator lens 149 matches a line parallel to the X-axis through the flow path 115 of the flow cell 110. The dichroic mirror 150 reflects the second side scattered light 222 in the Z-axis positive direction, and transmits the first side scattered light 212, first fluorescent light 213, and second fluorescent light 223.

The collective lens 151 converges the second side scattered light 222 reflected by the dichroic mirror 150. The optical detector 132 is a photodiode. The optical detector 132 outputs signals based on the second side scattered light which irradiates the light receiving part 132a. The spectral filter 152 absorbs the first side scattered light 212 and the second fluorescent light 223, and transmits the first fluorescent light 213. The collective lens 153 converges the first fluorescent light 213 which is transmitted through the spectral filter 152. The optical detector 133 is an avalanche photodiode. The optical detector 133 outputs signals based on the first fluorescent light 213.

The method of associating the first scattered light information and the second scattered light information is described below.

As described referring to FIG. 2B, the irradiation position 202 of the first light 210 and the irradiation position 203 of the second light 220 are mutually shifted in the Y-axis direction. The blood cells within the flow path 115 flow from the irradiation position 203 to the irradiation position 202. Accordingly, there is a predetermined timing from the irradiation of the blood cell by the second light 220 at the irradiation position 203, until the same blood cell is irradiated by the first light 210 at the irradiation position 202. When the first scattered light information based on the first forward scattered light 211 produced by the first light 210, and the second scattered light information based on the second forward scattered light 221 produced by the second light 220 are used in analysis, the first scattered light information and the second scattered light information produced from the same blood cell therefore must be mutually associated.

Figure 4A:
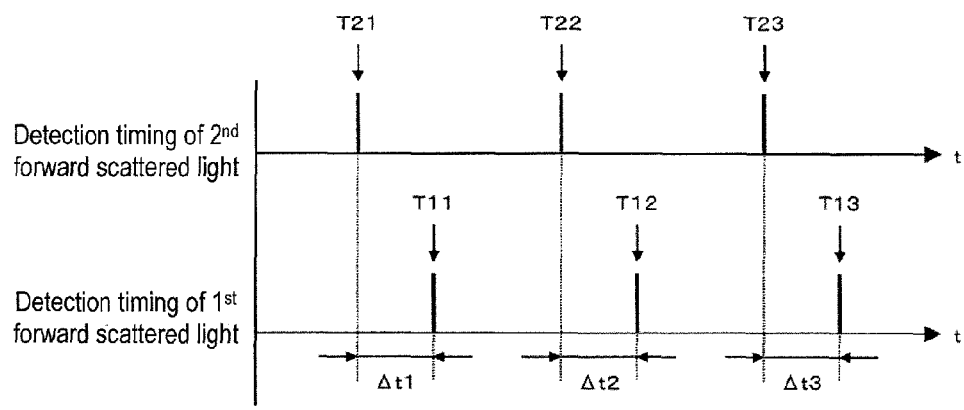
FIG. 4A illustrates detection timing when a low concentration first measurement sample is measured.

As shown in FIG. 4A, when a low concentration first measurement sample is measured, the detection timing of the second forward scattered light 221 and the detection timing of the first forward scattered light 211 become discrete. In this case the detection timing of the second forward scattered light 221 based on the next blood cell cannot be started during the interval between the detection timing of the second forward scattered light 221 and the detection timing of the first forward scattered light 211 based on a single blood cell. Accordingly, the detection timing of the first forward scattered light 211 arriving subsequent to the detection timing of the second forward scattered light 221 can be associated as a detection timing related to the same blood cell.

In the example of FIG. 4A, the detection timings T21 through T23 are respectively associated with the detection timings T11 through T13. The time differential of the detection timings based on the same blood cell is substantially the same whatever the blood cell. Accordingly, for example, the time differentials $\Delta t1$, $\Delta t2$, $\Delta t3$ of two mutually associated detection timings are obtained, and a time differential $\Delta t$ is calculated by averaging the time differentials. Hence, the time differential $\Delta t$ can be used as the time differential of the detection timings of the second forward scattered light 221 and the first forward scattered light 211 relative to each blood cell.

Figure 4B:
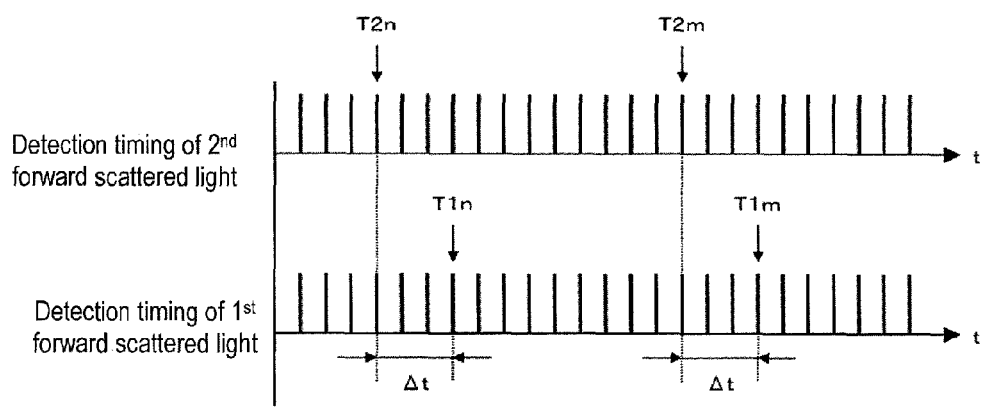
FIG. 4B illustrates detection timing when a normal concentration first measurement sample is measured.

As shown in FIG. 4B, when a normal concentration first measurement sample is measured, the detection timing of the second forward scattered light 221 and the detection timing of the first forward scattered light 211 are mixed. In this case it is difficult to associate the detection timing of the second forward scattered light 221 and the detection timing of the first forward scattered light 211 based on the same blood cell. However, the speed of the first measurement sample flowing through the flow cell 110 is approximately the same when the concentration is high and when the concentration is low. The time differential $\Delta t$ obtained when the concentration was low can be used as the time differential of the detection timing of the second forward scattered light 221 and the detection timing of the first forward scattered light 211 based on the same blood cell when concentration is high. In the example of FIG. 4B, the detection timings T2n and T2m are associated with the detection timings T1n and T1m, respectively, using the time differential $\Delta t$.

In the first embodiment, an advance time differential $\Delta t$ is obtained beforehand by flowing a low concentration sample through the flow cell 110 before performing a measurement; the second scattered light information and the first scattered light information based on the same blood cell are then sequentially associated using the time differential $\Delta t$ during the actual measurement. Similarly, the second scattered light information and the fluorescent light information based on the same blood cell are sequentially associated using the time differential Δt during the actual measurement. In this way all information based on the same blood cell can be associated by using the time differential Δt obtained beforehand.

The difference of the first forward scattered light 211 produced from red blood cells and the first forward scattered light 211 produced from blood cells other than red blood cells is described below. Blood cells other than red blood cells include white blood cells and platelets.

The scattered light produced from particles which are irradiated by light is determined by the particle diameter and refractive index according to the Mie scattering theory. The refractive index can be expressed by a complex number consisting of a real number part and an imaginary number part. That is, when the complex refractive index is designated m, the refractive index is designated nr, and the absorption is designated ni, the complex refractive index m can be calculated by the following equation.

$$m = nr + ini$$

According to the above equation, the refractive index may differ according to differences in the degree of absorption of the particle relative to light since the complex refractive index m changes according to the absorption ni. Thus, when different types of particles have mutually different degrees of absorption and these particles are irradiated by light, the resultant scattered light also will be mutually different.

Figure 5A:
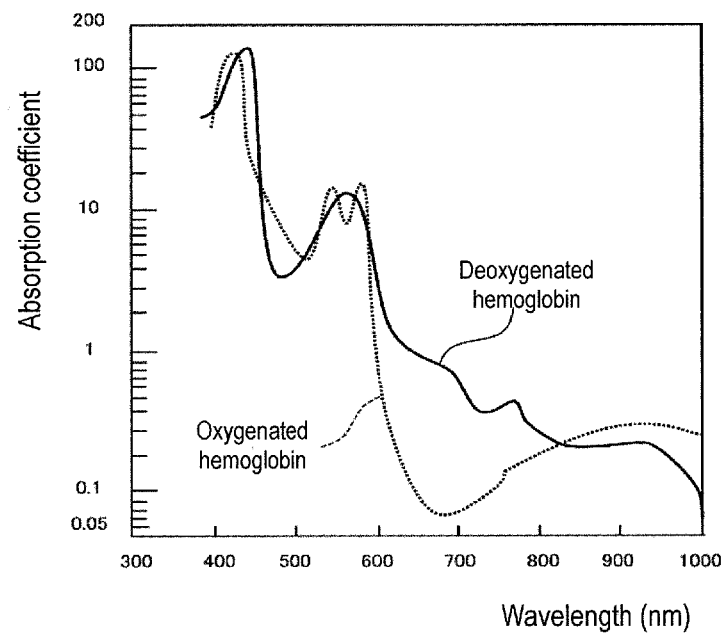
FIG. 5A shows the absorption characteristics of the hemoglobin contained in a red blood cell.

Hemoglobin which is contained in red blood cells has the absorption characteristics shown in FIG. 5A. In FIG. 5A, the horizontal axis represents the wavelength of the light irradiated on the hemoglobin, and the vertical axis represents the absorption coefficient. FIG. 5A shows the absorption coefficients of oxygenated hemoglobin and deoxygenated hemoglobin, respectively. The hemoglobin in red blood cells is a mixture of oxygenated hemoglobin and deoxygenated hemoglobin, and generally the oxygen saturation of venous blood hemoglobin is 75%, that is, content ratio of oxygenated hemoglobin to deoxygenated hemoglobin is 3:1. Therefore, the properties of oxygenated hemoglobin are dominant in red blood cells contained in the blood sample.

The absorption coefficient of oxygenated hemoglobin increases in several stages in the wavelength range of 400 nm or greater but not more than 435 nm compared to other wavelength bands. On one hand, the absorption coefficient of oxygenated hemoglobin decreases in several stages in the wavelength range of 610 nm or greater but not more than 700 nm compared to other wavelength bands. That is, there is a large difference in the degree of absorption of red blood cells relative to the first light 210 and the degree of absorption of red blood cells relative to the second light 220. On the other hand, there is a small difference in the degree of absorption of blood cells other than red blood cells relative to the first light 210 and the degree of absorption of blood cells other than red blood cells relative to the second light 220 because blood cells other than red blood cells do not contain hemoglobin.

From the above, there is a marked difference in the degree of absorption relative to the first light 210 and the degree of absorption relative to the second light 220 between red blood cells and blood cells other than red blood cells. Accordingly, there also is a difference in the intensity of the first forward scattered light 211 produced by irradiation with the first light 210 and the intensity of the second forward scattered light 221 produced by irradiation with the second light 220 between the red blood cells and the blood cells other than red blood cells. Specifically, in red blood cells the first forward scattered light is easily weaker than the second forward scattered light. In blood cells other than red blood cells the first forward scattered light and the second forward scattered light are easily substantially the same.

Figure 5B:
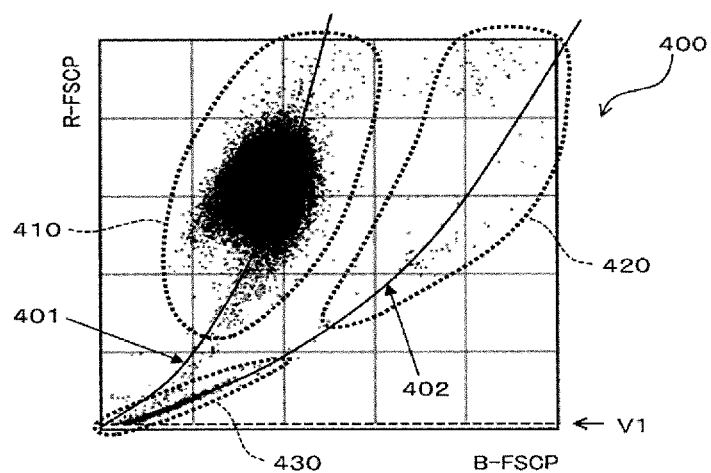
FIG. 5B shows is a scattergram for classifying red blood cells of the first embodiment.

In the first embodiment, red blood cells can be separated from other blood cells such as white blood cells and platelets by using regions 410, 420, and 430 set in the scattergram 400, as shown in FIG. 5B. Each blood cell is plotted in scattergram 400 based on the first scattered light information and second scattered light information obtained from each blood cell. The horizontal axis and vertical axis of the scattergram 400 respectively represent the first scattered light information and the second scattered light information. Regions 410, 420, and 430 are regions in which red blood cells, white blood cells, and platelets are distributed, respectively. The area in which the second scattered light information is less than a threshold value V1 in scattergram 400 is excluded.

As shown in FIG. 5B, red blood cells are distributed along a distribution curve 401, and white blood cells and platelets are distributed along a distribution curve 402. The distribution curve 401 representing the distribution of red blood cells is positioned on the left side of the distribution curve 402 representing the distribution of white blood cells and platelets for the reasons stated above. In actual measurement values, therefore, regions 410, 420, and 430 are unlikely to mutually overlap because the distribution curves 401 and 402 extend at mutually different angles without intersection. Hence, red blood cells can be accurately separated from other blood cells in the sample.

In iron deficiency anemia which is one type of microcytic anemia, red blood cells are smaller and the hemoglobin concentration in the red blood cells tends to be lower compared to normal. In thalassemia which is one type of microcytic anemia, red blood cells are smaller and the hemoglobin concentration in the red blood cells tends to be slightly lower compared to normal. Accordingly, determinations can be made related to the type of microcytic anemia based on the size of the red blood cells and the hemoglobin concentration.

The inventors considered making determinations regarding the type of microcytic anemia by using the scattergram 400. The scattered light information reflects the size of the blood cell and the hemoglobin concentration within the blood cell. However, in the scattergram 400, the second scattered light information on the vertical axis is more dominantly influenced by the size of the blood cell, and the first scattered light information on the horizontal axis is more dominantly influenced by the degree of absorption relative to the first light 210, that is, by the hemoglobin concentration within the blood cell. The region 410 in which red blood cells are distributed also does not overlap regions 420 and 430. However, the distribution condition of the red blood cells can be obtained by referencing region 410 in which red blood cells are distributed, and a determinations can be made regarding the type of microcytic anemia based on the distribution obtained condition of the red blood cells.

Differences in the condition of distribution of red blood cells on scattergram 400 according to the type of microcytic anemia, and the regions used to make determinations of the distribution condition are described referring to FIG. 6A through FIG. 6D. FIG. 6A through FIG. 6D show an area of small first scattered light information in the scattergram 400 for convenience.

As shown in FIG. 6A through FIG. 6D, a rectangular region 440 is set in scattergram 400 in the first embodiment. The region 440 corresponds to region 410 in which red blood cells are distributed in FIG. 5B. Region 440 is set based on region 410 of FIG. 5B. Region 440 is preferably identical to region 410. However, region 440 also may be set to include all or part of region 410, and all of region 440 may be set so as to include region 410. The shape of region 440 also may be non-rectangular.

Figure 6A:
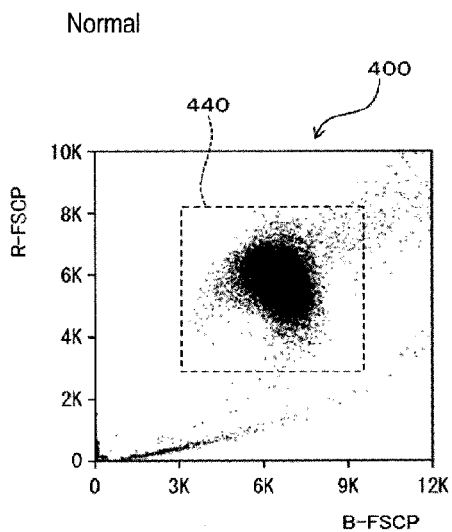
FIG. 6A through FIG. 6D respectively are scattergrams created based on normal blood samples, blood samples of iron deficiency anemia, blood samples of alpha-thalassemia, and blood samples of beta-thalassemia.
Figure 6B:
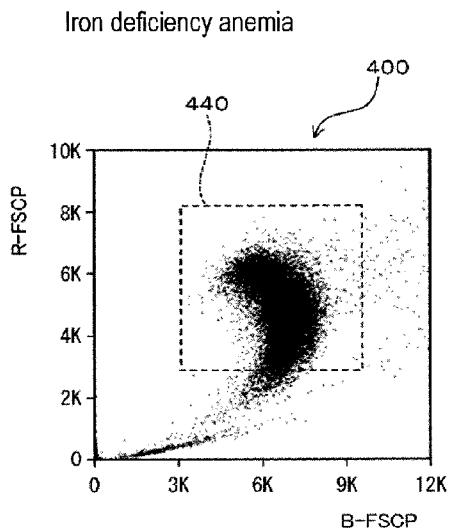
Figure 6C:
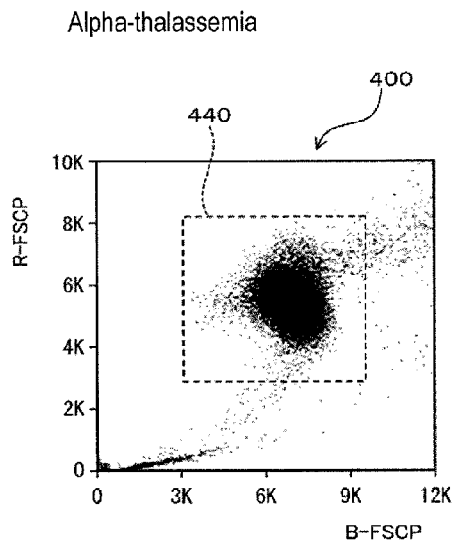
Figure 6D:
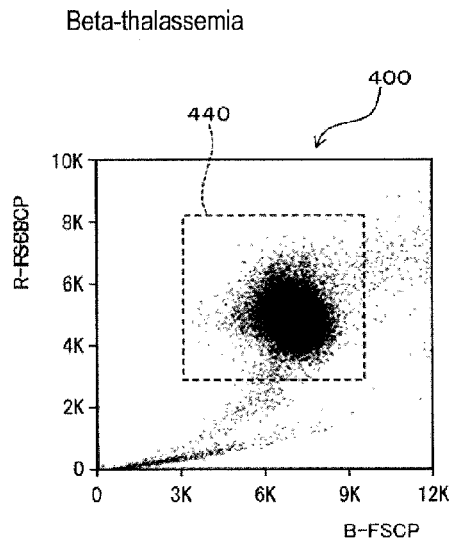

When referring to the interior of region 440 of FIG. 6A through FIG. 6D, it is understood that the shape of the distribution of red blood cells differs. As described above, this is due to the difference of the inclination between the size of the red blood cells and the hemoglobin concentration of the red blood cells. For example, the shape of the distribution in the normal blood sample shown in FIG. 6A is elliptical; the shape of the distribution of the iron deficiency anemia blood sample shown in FIG. 6B is crescent shaped, the shape of the distribution of the alpha-thalassemia blood sample shown in FIG. 6C and the shape of the distribution of the beta-thalassemia blood sample shown in FIG. 6D is substantially circular. In the iron deficiency anemia blood sample shown in FIG. 6B, there is a large spread in the vertical axis direction compared to the normal blood sample shown in FIG. 6A and the thalassemia blood samples shown in FIG. 6C and FIG. 6D. On the thalassemia blood samples shown in F FIG. 6C and FIG. 6D, the red blood cells are dispersed in a downward direction from near the center compared to the normal blood sample shown in FIG. 6A.

In the first embodiment, distribution information is obtained which represents the distribution condition of the red blood cells within the region 440, and determination are made regarding the type of microcytic anemia based on the obtained distribution information. The specific determinations are described below referring to FIG. 8A.

The process performed by the blood analyzer 10 is described below referring to FIG. 7 and FIG. 8A. Steps S11 through S19 of FIG. 7 are performed based on the control by the measurement controller 11, steps S21 through S25 of FIG. 7 and steps S101 through S106 of FIG. 8A are performed based on the control by the processing unit 21.

When the blood analyzer 10 starts, an advance time differential Δt is obtained as described referring to FIG. 4A and FIG. 4B. The obtained advance time differential Δt is stored in the memory unit 11a of the measuring unit 10a.

Figure 7:
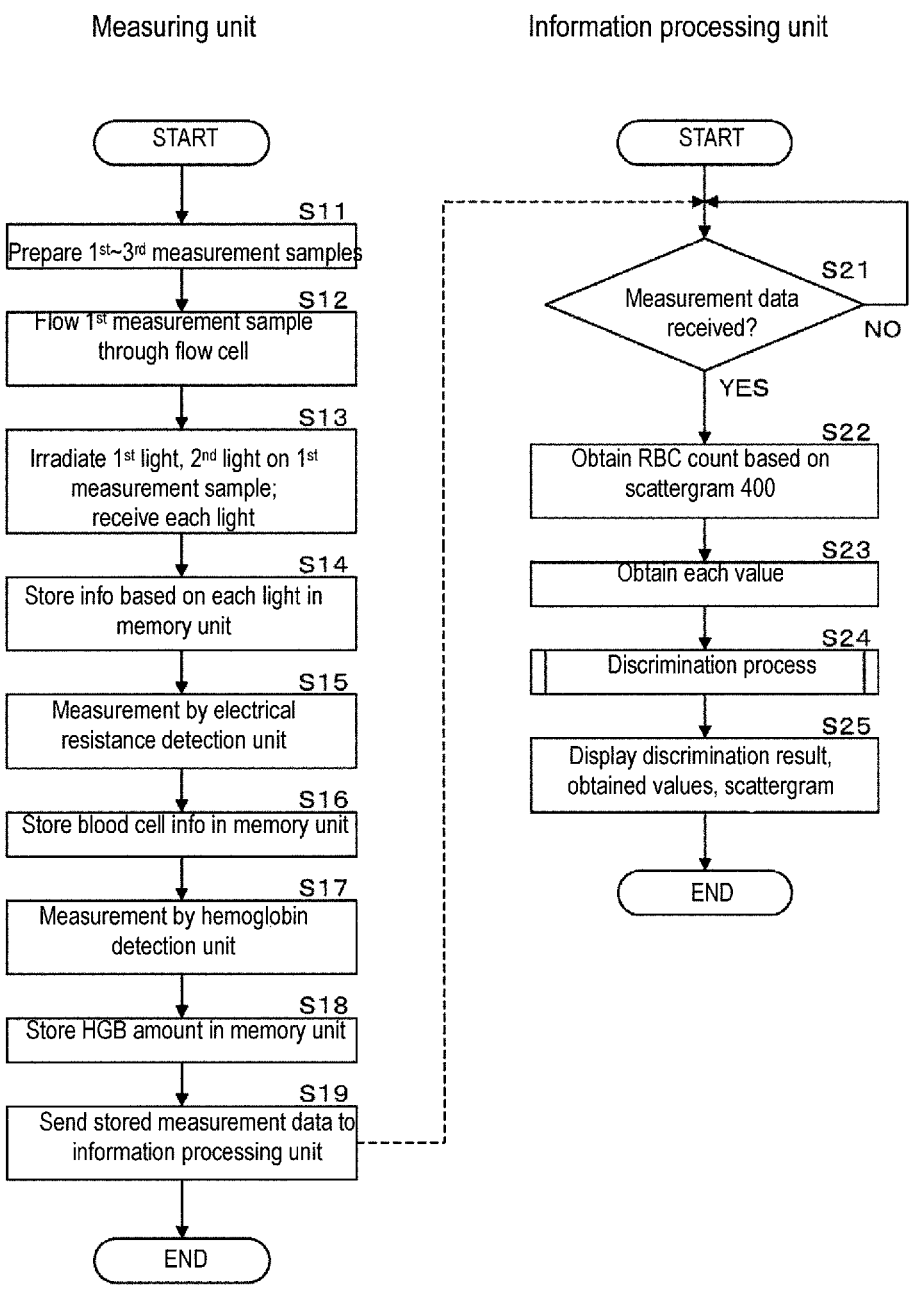
FIG. 7 is a flow chart showing the processes of the blood analyzer of the first embodiment.
Figure 8A:
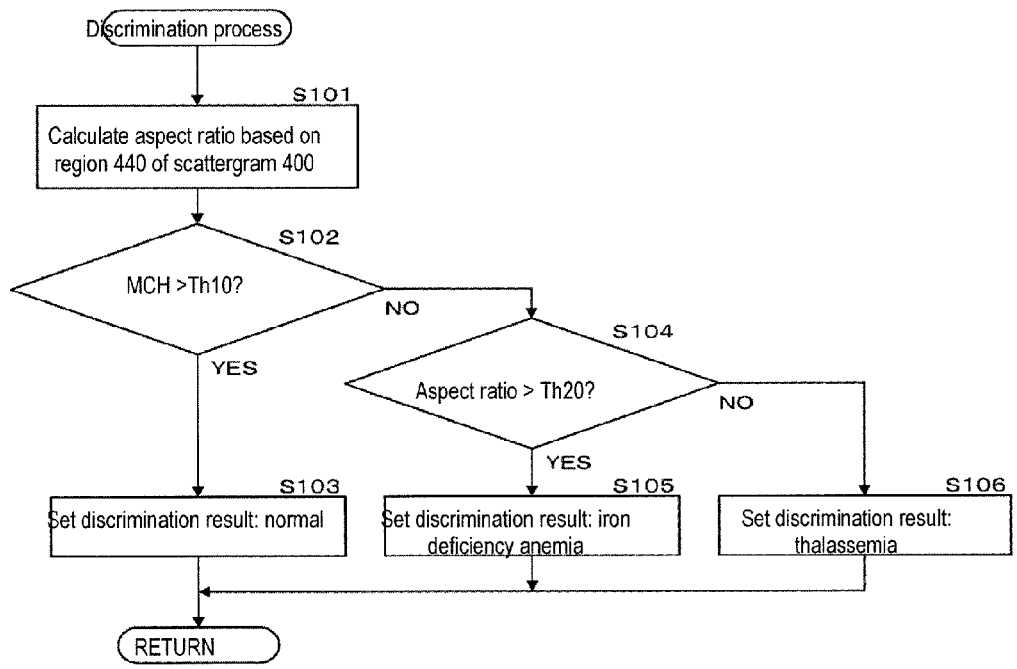
FIG. 8A is a flow chart showing the discrimination process of the first embodiment.

As shown in FIG. 7, in step S11 the first and second measurement samples are prepared by mixing blood sample and reagent 13a, and the third measurement sample is prepared by mixing blood sample and reagents 13a and 13b. The preparation of the first and second measurement samples is performed without mixing hemolytic agent and stain.

In step S12, the first measurement sample flows through the flow cell 110. In step S13, the first light 210 and the second light 220 irradiate the first measurement sample flowing through the flow cell 110. The first forward scattered light 211 and the first fluorescent light 213 obtained by irradiating blood cells flowing through the flow cell 110 with the first light 210 are received by the first light receiving part 131a and the fluorescent light detector 133. The second forward scattered light 221 and the second side scattered light 222 obtained by irradiating blood cells flowing through the flow cell 110 with the second light 220 are received by the second light receiving part 131b and the light receiving part 132a.

In step S14, the measurement controller 11 mutually associates the first scattered light information, second scattered light information, third scattered light information, and fluorescent light information produced from the same blood cell based on the time differential Δt, and stores the associated information in the memory unit 11a. When the second scattered light information is less than the threshold value V1 shown in FIG. 5B, each information is not stored in the memory unit 11 a. The threshold value V1 is set at a minute value.

In step S15, the second measurement sample is flowed through the sheath flow cell of the electrical resistance detection unit 16, and the blood cells are measured. In step S16, the measurement controller 11 stores the blood cell information in the memory unit 11a. In step S17, the third measurement sample is supplied to the hemoglobin detection unit 17, and the hemoglobin content is measured. In step S18, the measurement controller 11 stores the hemoglobin content in the memory unit 11a.

In step S19, the measurement controller 11 sends the measurement data stored in the memory unit 11a to the information processing unit 10b. The processes of steps S12 through S14, processes of steps S16 and S16, and processes of steps S17 and S18 also may be performed in parallel. When all measurements end, the process of step S19 is executed.

In step S21, the processing unit 21 determines whether measurement data have been received from the measuring unit 10a. When the determination is YES in step S21, the processing unit 21 counts the number of blood cells in regions 410 and obtains the red blood cell count in step S22 based on the scattergram 400 shown in FIG. 5B.

In step S22, for the convenience of the description, region 410 is set on scattergram 400, and the number of blood cells in region 410 is counted. However, scattergram 400 and region 410 need not necessarily be created inasmuch as the number of blood cells in region 410 also may be obtained by data processing.

The same applies to the following processes. That is, the scattergram 400 and region 440 need not necessarily be created in step S101 of FIG. 8A, inasmuch as the blood cells of region 440 also can be extracted through data processing, and the aspect ratio also may be obtained by data processing. Further, scattergram 400 and regions 451 and 452 need not necessarily be created in step S111 of FIG. 11 inasmuch as the number of blood cells in regions 451 and 452 also may be obtained by data processing. Even in step 5201 of FIG. 14C, the scattergram 700 need not necessarily be created inasmuch as each value also can be obtained through data processing.

Then, in step S23, the processing unit 21 also obtains each of the following values. Processing unit 21 obtains the red blood cell count RBC, an mean corpuscular volume MCV based on the blood cell information obtained in steps S15 and S16. The hemoglobin content obtained in steps S17 and S18 is designated HGB, and the processing unit 21 calculates the mean corpuscular hemoglobin MCH by HGB/RBC. RBC also may the red blood cell count obtained in step S22.

In step S24, the processing unit 21 executes the discrimination process shown in FIG. 8A. As shown in FIG. 8A, in step S101 the processing unit 21 creates the scattergrams 400 shown in FIG. 6A through FIG. 6D based on the obtained first scattered light information and second scattered light information, and sets the region 440 in the scattergram 400. The processing unit 21 then calculates the aspect ratio based on the region 440 as the distribution information representing the distribution condition.

Specifically, the processing unit 21 obtains the standard deviation of the first scattered light information for the blood cells within region 440 as a first value related to the dispersion of the distribution of red blood cells in the first scattered light information. The processing unit 21 obtains the standard deviation of the second scattered light information for the blood cells within region 440 as a second value related to the dispersion of the distribution of red blood cells in the second scattered light information. The processing unit 21 calculates the aspect ratio by dividing the second value by the first value. The aspect ratio reflects the shape of the distribution of red blood cells within region 440.

In step S102, the processing unit 21 determines whether the MCH calculated in step S23 is greater than a threshold value Th10. The threshold value Th10 is a threshold for determining whether the blood sample is either normal or microcytic anemia based on MCH. As described above, since there are fewer red blood cells and the hemoglobin concentration of red blood cells is low in microcytic anemia, whether a blood sample is microcytic anemia can be determined by the mean corpuscular hemoglobin MCH. When MCH is greater than the threshold value Th10 in step S102, the processing unit 21 determines the discrimination results to be normal in step S103 and the discrimination process ends.

In step S102, the processing unit 21 determines whether the MCV calculated in step S23 is greater than a threshold value Th11. The threshold value Th11 is a threshold for determining whether the blood sample is either normal or microcytic anemia based on MCV. As described above, since red blood cells tend to be smaller in microcytic anemia, whether a blood sample is microcytic anemia can be determined by the mean corpuscular volume MCV.

When the determination is NO in step S102, the processing unit 21 determines whether the aspect ratio is greater than a threshold value Th20 in step S104. The threshold value Th20 is a threshold for determining whether a blood sample is iron deficiency anemia based on aspect ratio. When the aspect ratio is determined to be greater than the threshold value Th20 in step S104, the processing unit 21 determines the discrimination results to be iron deficiency anemia in step S105 and the discrimination process ends. When the determination is NO in step S104, the processing unit 21 determines the discrimination results are thalassemia in step S106, and the discrimination process ends.

Thus, according to the first embodiment, distribution information, that is, the aspect ratio, is obtained based on the first scattered light information and the second scattered light information, and a determination is made regarding the type of microcytic anemia based on the obtained aspect ratio. When determination results regarding types of microcytic anemia are provided to physicians and the like, the physician can refer to the results in diagnosing factors of anemia.

In the discrimination process, the processing unit 21 also may calculate values other than the aspect ratio as distribution information representing the distribution condition, and make determinations regarding the types of microcytic anemia based on the calculated value. Since the shape of the distribution of red blood cells is different for each type of microcytic anemia as described referring to FIG. 6A through FIG. 6D, in the discrimination process the processing unit 21 also may make determinations regarding the types of microcytic anemia based on the shape of the distribution of red blood cells.

Figure 8B:
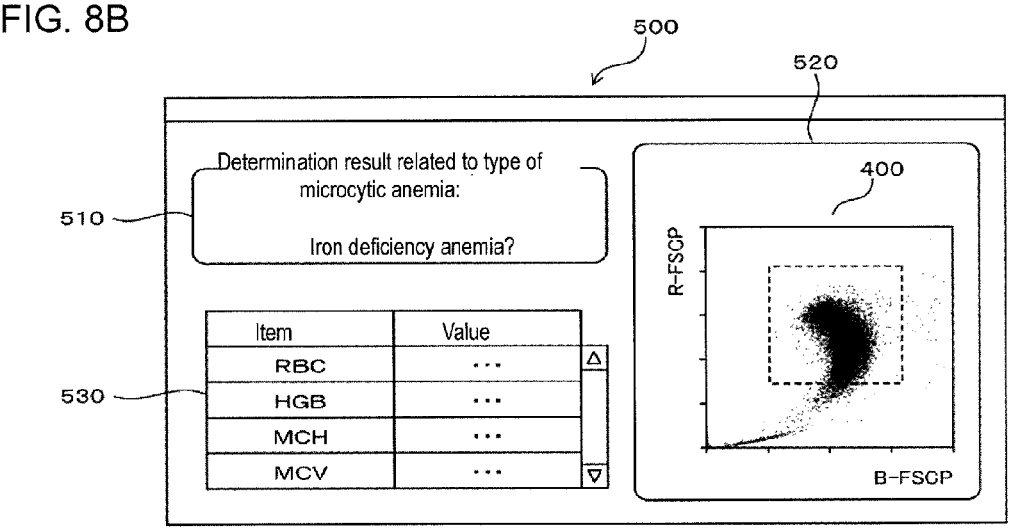
FIG. 8B shows a screen displayed on the output unit of the first embodiment.

Returning to FIG. 7, in step S24, the processing unit 21 displays a screen 500 shown in FIG. 8B on the output unit 22. The screen 500 includes regions 510 and 520, and a list 530. Region 510 shows the determination results regarding the type of microcytic anemia. "Normal" is displayed in region 510 when the discrimination result is normal, "iron deficiency anemia?" is displayed when the discrimination result is iron deficiency anemia, and "thalassemia?" is displayed when discrimination result is thalassemia. Region 520 shows the scattergram 400 based on the measured blood sample. The list 530 include values obtained in steps S22 and S23.

The operator can visually comprehend the discrimination results and measurement results by referring to screen 500. The screen 500 may include, not only scattergram 400 of two axes as shown in FIG. 8B, but also may include scattergrams of three axes by adding an axis for an additional parameter.

The relationship between aspect ratio and MCH relative to patient cases is described below referring to FIG. 9A.

In the following verification, 194 blood samples divided among four types of cases were used. Among the 194 blood samples, 71 were normal blood samples, 67 were blood samples of iron deficiency anemia, 26 were alpha-thalassemia blood samples, and 30 were beta-thalassemia blood samples. Measurements were performed by the blood analyzer 10 of the first embodiment on the 194 blood samples divided among these four types of cases, and the aspect ratio and MCH were calculated by the method described above. In the graph shown in FIG. 9A, the aspect ratio and MCH are set on the vertical axis and horizontal axis, respectively, and points corresponding to the 194 blood samples are plotted.

Figure 9B:
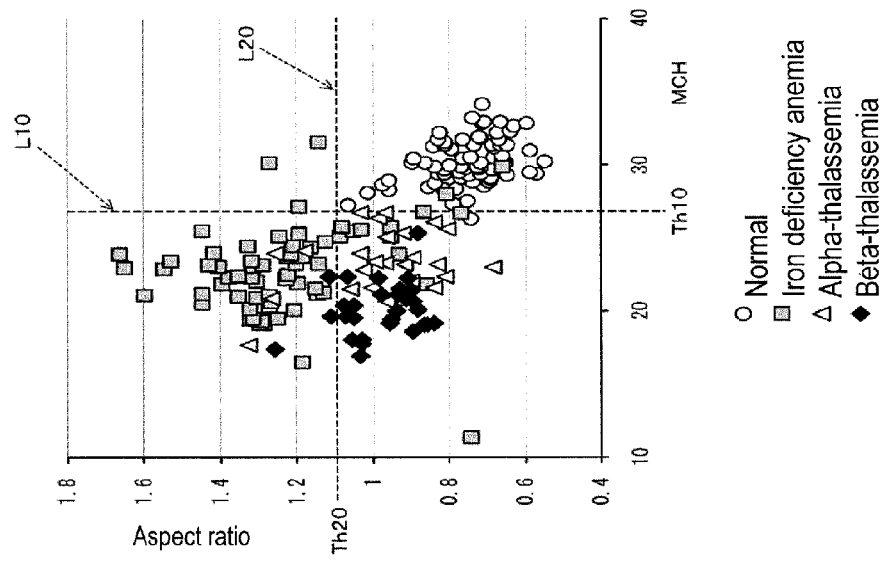
FIG. 9B illustrates a screen displayed on the output unit of the first embodiment.
Figure 9A:
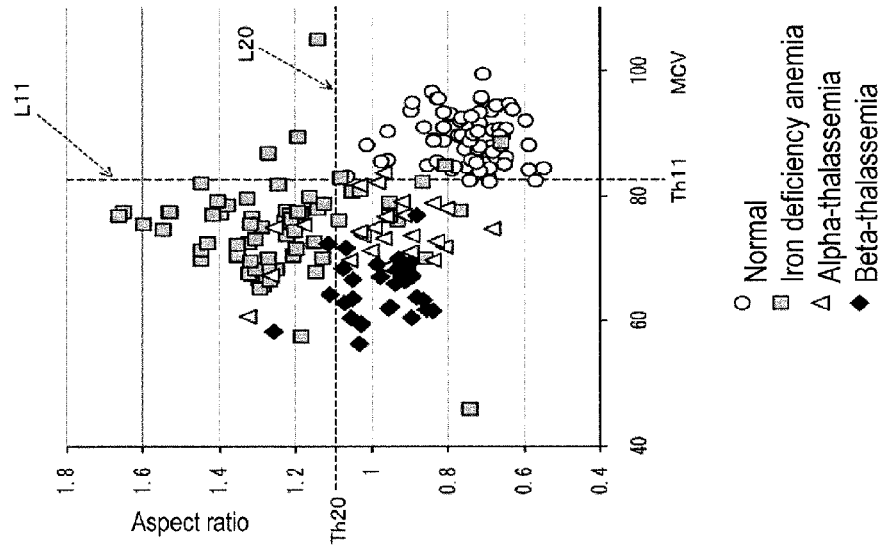
FIG. 9A illustrates the relationship of MCH and the aspect ratio in the first embodiment.
Figure 10A:
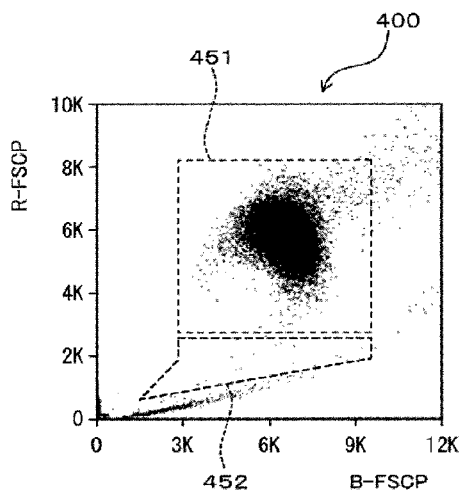
FIG. 10A through FIG. 10D respectively are scattergrams created based on normal blood samples, blood samples of iron deficiency anemia, blood samples of alpha-thalassemia, and blood samples of beta-thalassemia of the second embodiment.
Figure 10B:
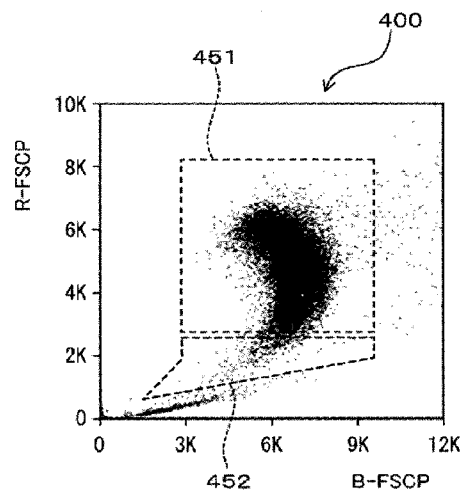
Figure 10C:
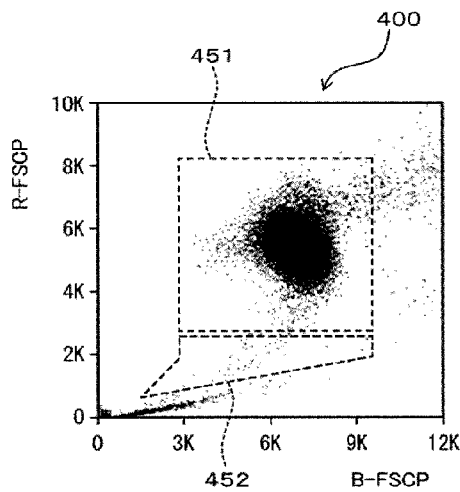
Figure 10D:
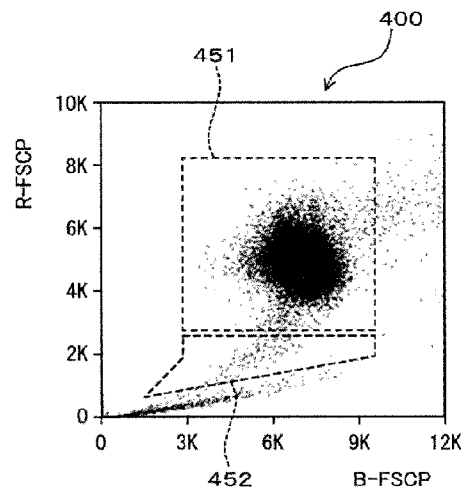

According to the graph in FIG. 9A, when a dashed line L10 corresponding to the threshold Th10 is set, it is understood that the normal blood samples tend to be distributed on the right side of the dashed line L10, whereas microcytic anemia blood samples tend to be distributed on the left side of the dashed line L10. When a dashed line L20 corresponding to the threshold Th20 is set, the iron deficiency anemia blood samples tend to be distributed above the dashed line L20, whereas the normal blood samples and thalassemia blood samples tend to be distributed below the dashed line L20.

Accordingly, the threshold Th10 used in step S102 of FIG. 8A is set as a value to distinguish between normal blood samples and microcytic anemia blood samples among the blood samples of several cases, as shown in FIG. 9A. The threshold Th20 used in step S104 of FIG. 8A is set as a value to distinguish between iron deficiency anemia blood samples, and normal blood samples and thalassemia blood samples among the blood samples of several cases, as shown in FIG. 9A. In this way, in the discrimination process of FIG. 8A, whether measured blood samples are normal blood samples, iron deficiency anemia blood samples, and thalassemia blood samples can be accurately determined.

As described above, MCV also may be used instead of MCH in the discrimination process. The graph shown in FIG. 9B switches the horizontal axis of the graph shown in FIG. 9A to MCV. The above 194 blood samples are plotted in the graph shown in FIG. 9B with the aspect ratio and MCV as parameters. In this case the MCV of each blood sample was obtained when the aspect ratio and MCH shown in FIG. 9A were calculated.

According to the graph in FIG. 9B, when a dashed line L11 corresponding to the threshold Th11 is set, it is understood that the normal blood samples tend to be distributed on the right side of the dashed line L11, whereas microcytic anemia blood samples tend to be distributed on the left side of the threshold value Th11 similar to FIG. 9A. However, the distribution region in which the blood samples of iron deficiency anemia are distributed and the distribution region in which the normal blood samples are distributed approach one another in the horizontal axis direction in the graph of FIG. 9B compared to FIG. 9A. Therefore, when MCH is used instead of MCV in step S102 of FIG. 8B, there is concern that the accuracy of the discrimination results may be slightly lower. It therefore is desirable to use MCH in step S102 of FIG. 8B.

Second Embodiment

In the second embodiment, the structure of the blood analyzer 10 is identical to that of the first embodiment, and only the discrimination process performed by the blood analyzer 10 is changed from that of the first embodiment.

As shown in FIG. 10A through FIG. 10D, regions 451 and 452 are set in scattergram 400 in the second embodiment. The scattergram 400 of FIG. 10A through FIG. 10D is the same scattergram 400 as FIG. 6A through FIG. 6D. Region 451 is set identically to region 440 of FIG. 6A through FIG. 6D. Region 452 is set below the region 451 to match the dispersion of red blood cells.

When referring to the interior of regions 452 of FIG. 10A through FIG. 10D, it is understood that the distribution condition of red blood cells differs in each. For example, in the iron deficiency anemia blood samples shown in FIG. 10B, many of the red blood cells are within region 452 compared to the normal blood sample shown in FIG. 10A and the thalassemia blood samples shown in FIG. 10C and FIG. 10D. In the blood samples of thalassemia shown in FIG. 10C and FIG. 10D, many of the red blood cells are within region 452 compared to the normal blood samples shown in FIG. 10A, although fewer red blood cells are within region 452 compared to the blood samples of iron deficiency anemia shown in FIG. 10B. In the second embodiment, distribution information is obtained which represents the distribution condition of the red blood cells within the region matching region 451 and region 452, and determinations are made regarding the type of microcytic anemia based on the obtained distribution information.

Figure 11:
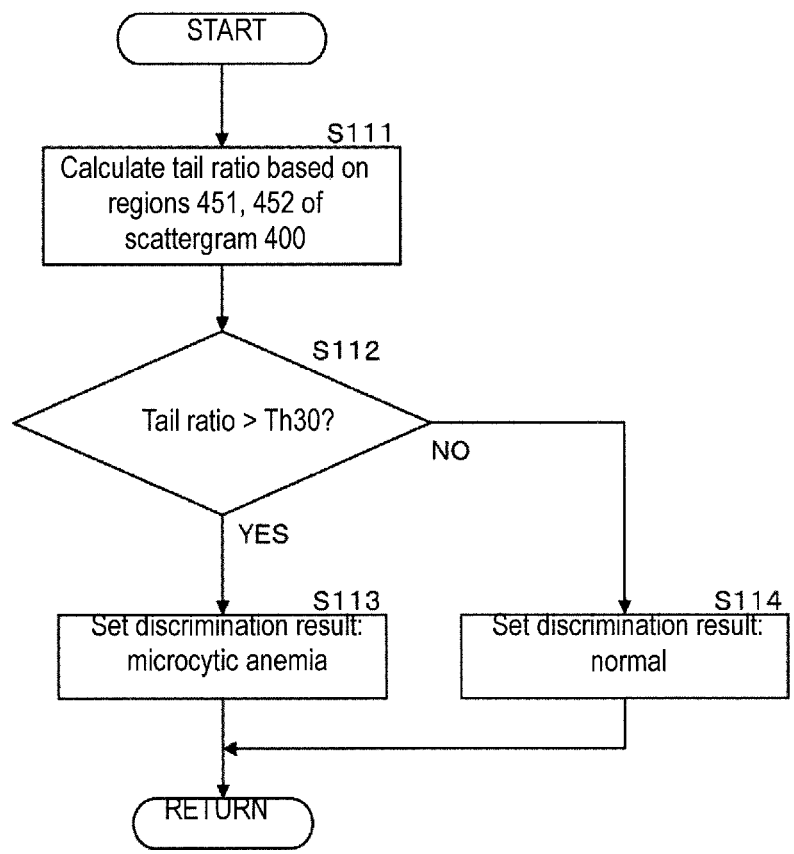
FIG. 11 is a flow chart showing the processes of the blood analyzer of the second embodiment.

The discrimination process of the second embodiment is described referring to FIG. 11.

In step S111 the processing unit 21 creates the scattergrams 400 shown in FIG. 10A through FIG. 10D based on the obtained first scattered light information and second scattered light information, and sets the regions 451 and 452 in the scattergrams 400. The processing unit 21 then calculates the tail ratio based on the regions 451 and 452 as the distribution information representing the distribution condition. When the red blood cell count within region 451 is designated N1 and the red blood cell count within region 452 is designated N2, the tail ratio is calculated by N2/(N1+N2). The tail ratio reflects the shape of the red blood cell distribution within the region which combines region 451 and region 452.

In step S112, the processing unit 21 determines whether the tail ratio is greater than a threshold Th30. The threshold value Th30 is a threshold for determining whether a blood sample is microcytic anemia based on the tail ratio. When the tail ratio is determined to be greater than the threshold value Th30 in step S112, the processing unit 21 determines the discrimination results to be microcytic anemia in step S113 and the discrimination process ends. When the determination is NO in step S112, the processing unit 21 determines the discrimination results are normal in step S114, and the discrimination process ends. "Normal" is displayed in region 510 of screen 500 shown in FIG. 8B when the discrimination result is normal, and "microcytic anemia?" is displayed when the discrimination result is microcytic anemia.

In this way, according to the second embodiment, a tail ratio is obtained as the ratio of small red blood cells based on the first scattered light information and the second scattered light information, and a determination can be made regarding whether it is microcytic anemia based on the obtained tail ratio.

The relationship between tail ratio and MCH relative to patient cases is described below referring to FIG. 12A.

Figure 12A:
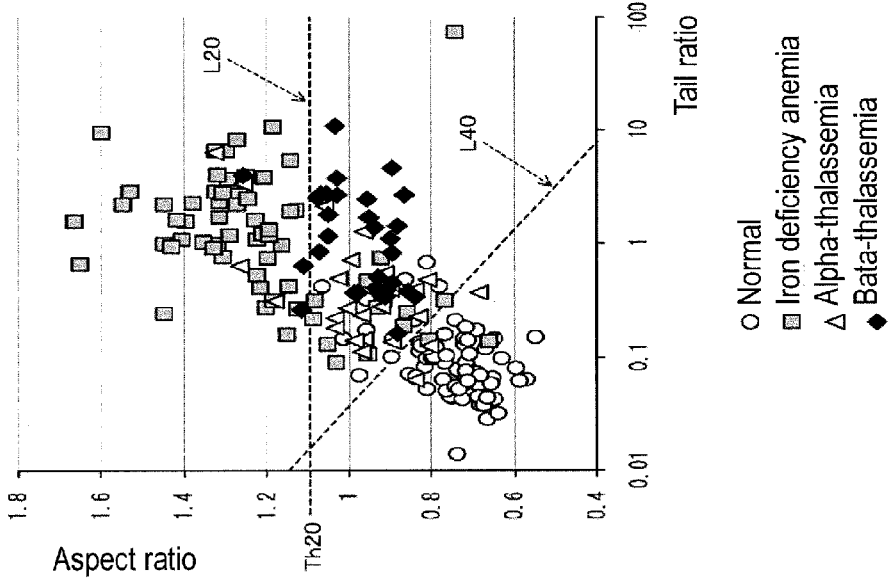
FIG. 12A illustrates the relationship of MCH and the tail ratio in the second embodiment.

The graph shown in FIG. 12A switches the vertical axis of the graph shown in FIG. 9A to tail ratio. In the graph shown in FIG. 12A, the tail ratio and MCH are set on the vertical axis and horizontal axis, respectively, and points corresponding to the 194 blood samples are plotted.

According to the graph in FIG. 12A, when a dashed line L30 corresponding to the threshold Th30 is set, it is understood that the normal blood samples tend to be distributed on the bottom side of the dashed line L30, whereas microcytic anemia blood samples, that is, blood samples of iron deficiency anemia and blood samples of thalassemia, tend to be distributed on the top side of the dashed line L30. Accordingly, the threshold Th30 used in step S112 of FIG. 11 is set as a value to distinguish between normal blood samples and microcytic anemia blood samples among the blood samples of several cases, as shown in FIG. 12A. In this way, in the discrimination process of FIG. 11, whether measured blood samples are normal blood samples or microcytic anemia blood samples can be accurately determined.

Both aspect ratio and tail ratio also can be used in the discrimination process. The graph shown in FIG. 12B switches the horizontal axis of the graph shown in FIG. 9A to tail ratio. In the graph shown in FIG. 12B, the aspect ratio and tail ratio are set on the vertical axis and horizontal axis, respectively, and points corresponding to the 194 blood samples are plotted.

Figure 12B:
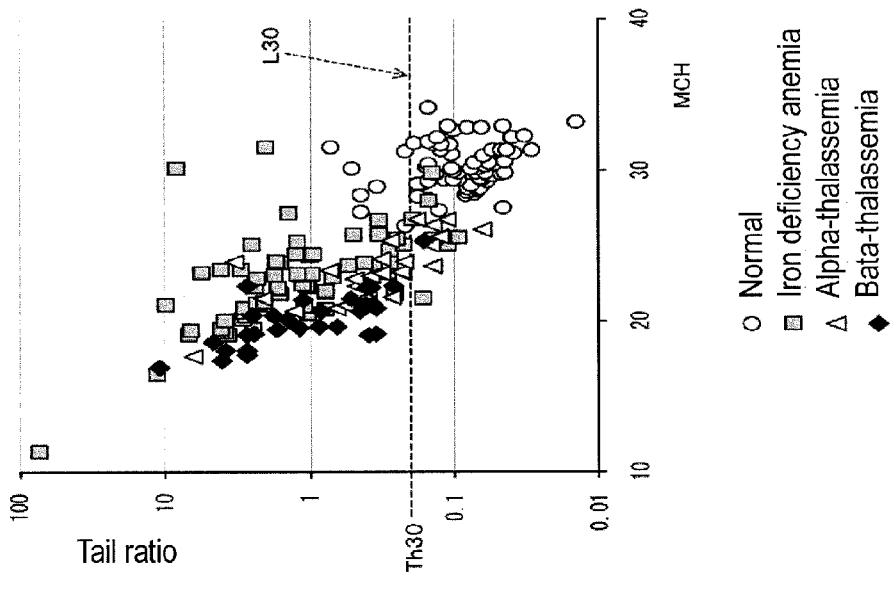
FIG. 12B illustrates the relationship of the aspect ratio and tail ratio in a modification of the second embodiment.

According to the graph in FIG. 12B, when a dashed line L40 extending in an inclined direction is set, it is understood that the normal blood samples tend to be distributed on the lower left of the dashed line L40, whereas microcytic anemia blood samples tend to be distributed on the upper right of the dashed line L40. Blood samples of iron deficiency anemia, and normal blood samples and thalassemia blood samples can be distinguished according to the dashed line L20 corresponding to the threshold Th20. Accordingly, whether measured blood samples are normal blood samples, iron deficiency anemia blood samples, and thalassemia blood samples can be determined by the discrimination process using the aspect ratio and tail ratio.

Third Embodiment

In the third embodiment, reagent 13b, electrical resistance detection unit 16, and hemoglobin detection unit 17 are omitted compared to the first embodiment. In the third embodiment, the structure of the blood analyzer 10 is otherwise identical to that of the first embodiment, and the processing performed by the blood analyzer 10 is partially changed from that of the first embodiment as will be described below. In the third embodiment, a scattergram 400 identical to FIG. 5B is created based on the detection signals of the optical detection unit 14. Then a scattergram 700 (described below) is created based on scattergram 400, and MCH, MCV, and HGB are obtained based on scattergram 700.

A simulation of the particle analysis is described below.

The present simulation was performed under the following conditions. The NA of the optical system receiving the forward scattered light is set at NA=0.22. An optical system provided with the collective lens 146, beam stopper 147, pinhole 148, and optical detector 131 was used as the optical system which receives the forward scattered light. The light shield part 147c of the beam stopper 147 has a width of 0.3 mm in the X-axis direction. The distance between the flow cell 110 and the beam stopper 147 was 6 mm. The first light 210 and the second light 220 which irradiate the flow cell 110 had a width of 10 μm in the Y-axis direction. In the present simulation, 81 cell-like particles having the same characteristics as red blood cells and 4 cell-like particles having the same characteristics as platelets were set. The intensities of the forward scattered light produced by irradiating laser light of a predetermined wavelength on these particles was calculated by the simulation.

In the present simulation particles corresponding red blood cells and platelets were irradiated with a first light 210 at a wavelength of 405 nm, and a second light 220 at a wavelength of 640 nm. The first scattered light information and the second scattered light information corresponding to each particle obtain in this way were plotted on scattergram 600 shown in FIG. 13. The horizontal axis and vertical axis of the scattergram 600 respectively represent the first scattered light information and the second scattered light information.

Then, a map 610 was created on the scattergram 600 based on the particles corresponding to red blood cells. The two axes of map 610 are the red blood cell volume and hemoglobin concentration. The map 610 is created based on the values of red blood cell volume V30 through V150 and the values of hemoglobin concentration HC22 through HC 46 for 81 individual particles. The intersection points of the grid of map 610 are the positions at which each particle was plotted. The map 610 corresponds to the range of red blood cell distribution. For the red blood cells of healthy persons, the red blood cell volume is V60 through V120 and the hemoglobin concentration is HC31 through HC37. Then, a distribution line 620 was created on the map 610 based on the particles corresponding to platelets. The distribution line 620 is created based on four particles having a volume value from V0.5 through V33.

From the results of the present simulation the red blood cells collected from subjects can be considered to be distributed within the map 610, and the platelets collected from subjects can be considered to be on the distribution line 620. The distribution line 620 and the extended line 621 of the distribution line 620 correspond to the distribution curve 402 shown in FIG. 5B.

Figure 13:
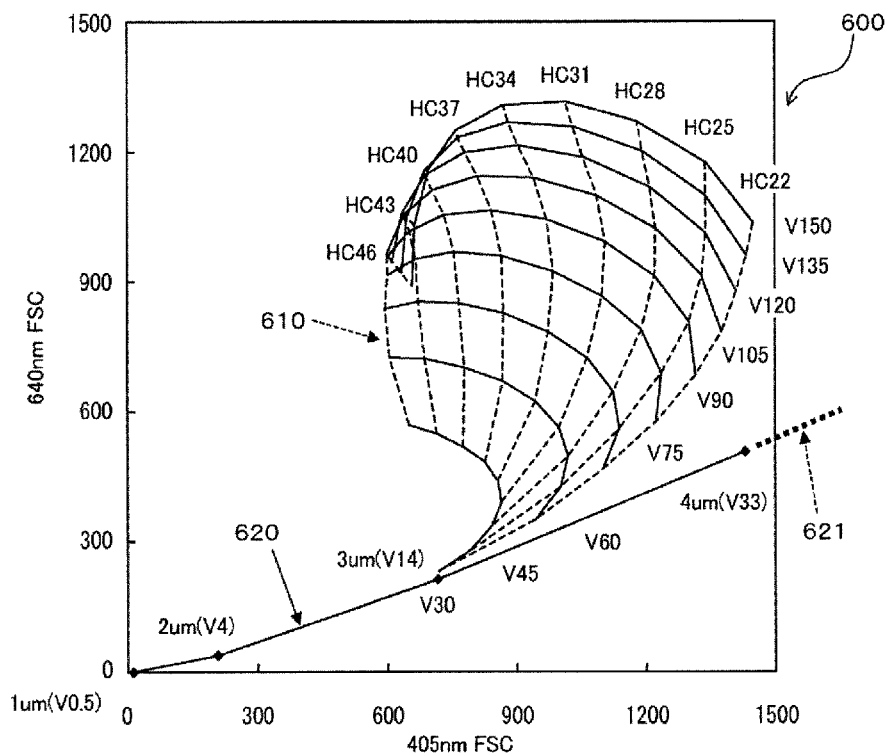
FIG. 13 shows simulation results of particle analysis.
Figure 14A:
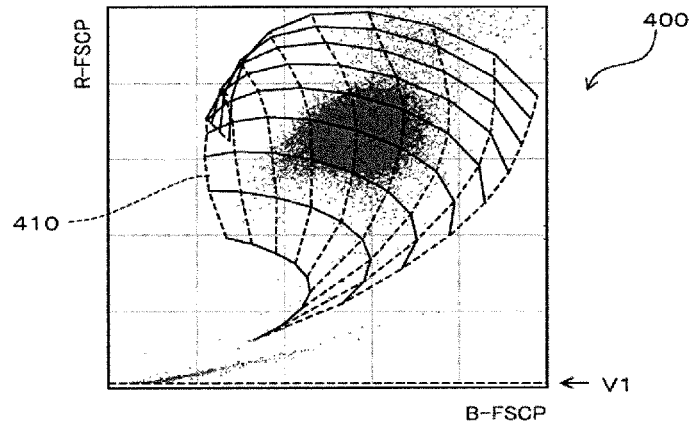
FIG. 14A is a scattergram which combines the map information in a third embodiment.

The map 610 shown in FIG. 13 was created based on 81 individual particles which had similar properties as red blood cells, red blood cell volume values of V30 through V150, and hemoglobin concentration values of HC22 through HC46. Accordingly, the red blood cell volume and hemoglobin concentration can be obtained for each blood cell within region 410 by combining the map information representing red blood cell volume and hemoglobin concentration in the region 410 which corresponds to red blood cells in the scattergram 400, as shown in FIG. 14A. Note that FIG. 14A shows an area in which the first scattered light information is small in the scattergram 400 of FIG. 5B.

Specifically, the region 410 which includes map information is applied to the scattergram 400 obtained by actual measurements is applied, as shown in FIG. 14A. Region 410 is developed together with blood cells contained in region 410 to create the scattergram 700 shown in FIG. 14B, and the red blood cell volume and hemoglobin concentration is obtained for each blood cell based on the plot position on the scattergram 700. In scattergram 700, the horizontal axis represents the hemoglobin concentration and the vertical axis represents the red blood cell volume.

More specifically, the memory unit 21a of the processing unit 21 stores the conversion information. The conversion information is configured from a conversion table and conversion program. The conversion table is a table representing the 81 individual intersection points within the region 410 shown in FIG. 14A plotted at positions in the scattergram 700 shown in FIG. 14B. The conversion program is a program configured to convert particles positioned between the intersection points of region 410 shown in FIG. 14A to positions on the scattergram 700 based on the distance to the intersection point. That is, the conversion information is information regulating the relationship between the combination of the first scattered light information and second scattered light information, and the combination of the red blood cell volume and hemoglobin concentration. The processing unit 21 obtains the red blood cell volume and the hemoglobin concentration from the first scattered light information and the second scattered light information using the conversion information.

Figure 14B:
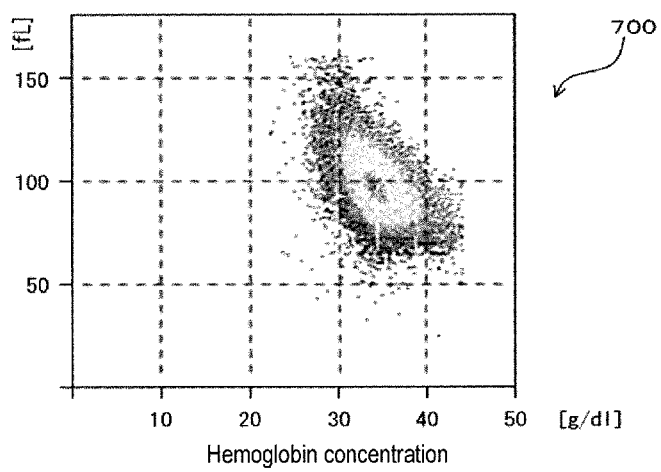
FIG. 14B is a scattergram plotting red blood cell volume and hemoglobin concentration on two axes.
Figure 14C:
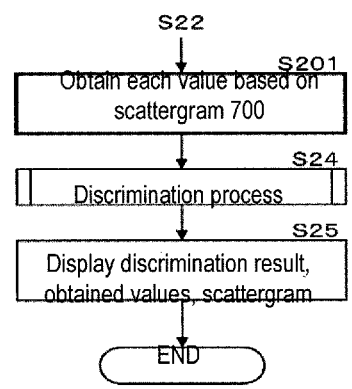
FIG. 14C is a flow chart showing the process of the blood analyzer of the third embodiment.

As shown in FIG. 14C, the process of the blood analyzer 10 of the third embodiment adds a step S201 min replacement of step S23 compared to FIG. 7.

In step S201, the processing unit 21 converts region 410 of scattergram 400 to scattergram 700 shown in FIG. 14B using the conversion information. The processing unit 21 obtains the red blood cell volume and hemoglobin concentration for each red blood cell in the region 410 in this way.

In step S201, the processing unit 21 also obtains each of the following values. The processing unit 21 determines the mean corpuscular volume (MCV) and mean corpuscular hemoglobin concentration (MCHC) using the red blood cell count obtained in step S22 as RBC. The MCV is calculated by dividing the total red blood cell volume of all particles in the scattergram 700 by the RBC. The MCHC is calculated by dividing the total hemoglobin concentration of all particles in the scattergram 700 by the RBC. The processing unit 21 calculates mean corpuscular hemoglobin (MCH) by MCV×MCHC. The processing unit 21 calculates hematocrit value (HCT) by MCV×RBC. The processing unit 21 calculates hemoglobin content (HGB) by HCT×MCHC.

In step S24, the processing unit 21 executes the discrimination process shown in FIG. 8A using the MCH obtained in step S201. The processing unit 21 uses the MCV obtained in step S201 even when the discrimination process is performed using the MCH instead of MCV. The scattergram 400 shown in FIG. 14A and the scattergram 700 shown in FIG. 14B also may be displayed together in screen 500 which is displayed in step S25.

The third embodiment obtains discrimination results identical to those of the first embodiment. Since the electrical resistance detection unit 16 and hemoglobin detection unit 17 are omitted, the blood analyzer 10 is more compact. Since discrimination results are obtained without using hemolytic agent or staining agent, the costs associated with measurements are reduced.

What is claimed is:
1. A blood analyzer comprising:
a flow cell configured to flow a sample containing blood cells therethrough;
a first light source configured to irradiate light of a first wavelength on the sample flowing through the flow cell;
a second light source configured to irradiate light of a second wavelength which is different from the first wavelength on the sample flowing through the flow cell;

a first light detector configured to detect the light of the first wavelength scattered from a respective blood cell and convert the first detected scattered light into a first scattered light value;

a second light detector configured to detect the light of the second wavelength scattered from the respective blood cell and convert the second detected scattered light into a second scattered light information; and a processor which executes a stored program which configures the processor to:

store respectively in the memory, the first and second scattered light values in pairs to each represent the respective blood cell in the sample;

determine a configuration of distribution of the stored pairs of first and second scattered light values;

discriminate a type of microcytic anemia based on the determination of the configuration of the distribution of the stored pairs of first and second scattered light values.

2. The blood analyzer of claim 1, wherein the first light source irradiates light at a wavelength of 400 nm or greater but no more than 435 nm, and the second light source irradiates light at a wavelength of 610 nm or greater but no more than 750 nm.

3. The blood analyzer of claim 1, wherein the processor is programmed to determine the configuration of the distribution of the stored pairs of first and second scattered light values on a scattergram based on a first value representing the dispersion of the first scattered light values, and a second value representing the dispersion of the second scattered light values.

4. The blood analyzer of claim 3, wherein the processor is configured to discriminate the type of microcytic anemia based on the ratio of the first value and the second value.

5. The blood analyzer of claim 1, wherein the processor is configured to discriminate an iron deficiency anemia based on the determination of the configuration of the distribution of the stored pairs of first and second scattered light values.

6. The blood analyzer of claim 1, wherein the processor is configured to discriminate thalassemia based on the determination of the configuration of the distribution of the stored pairs of first and second scattered light values.

7. The blood analyzer of claim 1, wherein the processor is configured to determine the proportion of small sized red blood cells based on the first and the second scattered light values, and discriminate the type of microcytic anemia based on the obtained proportion.

8. The blood analyzer of claim 1, further comprising:
an output unit;
wherein the processor is configured to control the output unit to output the discrimination result regarding a type of microcytic anemia, and a scattergram having the first and the second scattered light value axis.

9. The blood analyzer of claim 1, wherein the first scattered light value represents a size of respective blood cell dominant over a hemoglobin concentration thereof; and the second scattered light value represents hemoglobin concentration dominant over the size of thereof.

10. The blood analyzer of claim 1, wherein the processor is configured to:
apply a filter to the stored pairs each representing respective blood cell in the sample.

11. The blood analyzer of claim 1, wherein the processor is configured to:
convert the configuration of the distribution of the stored pairs of first and second scattered light values into a numerical value.

12. The blood analyzer of claim 11, wherein the processor is configured to:
relate the numerical value to a specific type of microcytic anemia selected among a plurality of types of microcytic anemia.

13. The blood analyzer of claim 12, wherein the plurality of types of microcytic anemia comprise iron deficiency anemia and thalassemia.

14. The blood analyzer of claim 1, further comprising at least one of (i) a hemoglobin concentration detector configured to optically measure a hemoglobin concentration of respective red blood cell contained in the blood cells and (ii) a red blood cell volume detector configured to electrically measure a volume of respective red blood cell contained in the blood cells.

15. The blood analyzer of claim 14, wherein the processor is configured to:
count the stored pairs of first and second scattered light values representing the red blood cells in the blood cells to obtain a count of the red blood cells in the sample;
sum (i) measurements of the hemoglobin concentrations of the red blood cells by the hemoglobin concentration detector or (ii) measurements of volumes of the red blood cells by the red cell volume detector to obtain a total measurement of the red blood cells in the sample;
divide the total measurement of the red blood cells by the count of the red blood cells to obtain a mean measurement of the red blood cells in the sample; and
compare the mean measurement of the red blood cells with a threshold to notify whether the red blood cells in the sample are normal or suffer microcytic anemia.

16. A blood analyzing method comprising:
flowing a sample containing blood cells through a flow cell;
irradiating the blood cells flowing through the flow cell with a light having first wavelength and a light having second wavelength which is different from the first wavelength;
detecting lights of the first wavelength and the second wavelength scattered from a respective blood cell;
storing in the memory the first and second scattered light values in pairs each representing a respective blood cell in the sample;
determining a configuration of the distribution of the stored pairs of first and second scattered light values;
discriminate a type of microcytic anemia based on the determination of the configuration of the distribution of the stored pairs of first and second scattered light values.

* * * * *